(12) United States Patent
Diaz

(10) Patent No.: US 10,117,828 B1
(45) Date of Patent: Nov. 6, 2018

(54) ANTI-AGING MOISTURIZING EMULSION

(71) Applicant: DR. DS' FORMULAS INC., Miami Shores, FL (US)

(72) Inventor: Maria Diaz, Miami Shores, FL (US)

(73) Assignee: DR. DS' FORMULAS INC., Miami Shores, FL (US)

( * ) Notice: Subject to any disclaimer, the term of this patent is extended or adjusted under 35 U.S.C. 154(b) by 0 days.

(21) Appl. No.: 15/687,448

(22) Filed: Aug. 26, 2017

(51) Int. Cl.
| | |
|---|---|
| *A61K 8/98* | (2006.01) |
| *A61K 8/9794* | (2017.01) |
| *A61K 8/9789* | (2017.01) |
| *A61K 8/06* | (2006.01) |
| *A61K 8/26* | (2006.01) |
| *A61K 8/55* | (2006.01) |
| *A61Q 19/08* | (2006.01) |

(52) U.S. Cl.
CPC ............... *A61K 8/986* (2013.01); *A61K 8/06* (2013.01); *A61K 8/26* (2013.01); *A61K 8/553* (2013.01); *A61K 8/9789* (2017.08); *A61K 8/9794* (2017.08); *A61Q 19/08* (2013.01); *A61K 2800/5922* (2013.01)

(58) Field of Classification Search
None
See application file for complete search history.

(56) References Cited

U.S. PATENT DOCUMENTS

| | | |
|---|---|---|
| 6,544,530 B1 | 4/2003 | Friedman |
| 8,470,350 B2 | 6/2013 | Gervasio |
| 8,551,509 B2 | 10/2013 | Aoki et al. |
| 8,557,264 B2 | 10/2013 | Grune et al. |
| 2003/0190336 A1 | 10/2003 | Adams et al. |
| 2006/0024339 A1 | 2/2006 | Murad |
| 2006/0286046 A1 | 12/2006 | Haber |
| 2013/0171283 A1 | 7/2013 | Florence |
| 2013/0225497 A1 | 8/2013 | Kato et al. |
| 2013/0236402 A1 | 9/2013 | Wiedmann et al. |
| 2013/0261036 A1 | 10/2013 | Holscher |
| 2014/0018328 A1 | 1/2014 | Harrison et al. |

FOREIGN PATENT DOCUMENTS

| | | | |
|---|---|---|---|
| CN | 102772624 A | 11/2012 | |
| CN | 102784092 A | 11/2012 | |
| CN | 103330668 A | 10/2013 | |
| GB | 1051461 | 12/1966 | |
| KR | 100305011 B1 | 12/2001 | |
| WO | WO-2013149323 A1 * | 10/2013 | ............. A61Q 19/08 |

OTHER PUBLICATIONS

Ahshawat, M.S. et al., Preparation and Characterization of Herbal Creams for Improvement of Skin Viscoelastic Properties, International Journal of Cosmetic Science, 2008, vol. 30, pp. 183-193.
Brinkhaus, B. et al., Chemical, Pharmacological and Clinical Profile of the East Asian Medical Plant Centella asiatica, Phytomedicine, vol. 7(5), pp. 427-448.
Bylka, W. et al., Centella asiatica in Cosmetology, Postep Derm Alergol 2013; XXX, 1: pp. 46-49.
Garcia Hernandez, J.A., et al., Use of a Specific Anti-Stretch Mark Cream for Preventing or Reducing the Severity of Striae Gravidarum. Randomized, Double-Blind, Controlled Trial, International Journal of Cosmetic Science, 2013, vol. 35, pp. 233-237.
Maramaldi, G. et al., Anti-Infiammaging and Antiglycation Activity of a Novel Botanical Ingredient From African Biodiversity (Centevita™), Clinical, Cosmetic and Investigational Dermatology, 2014, vol. 7, pp. 1-9.
Martelli, L. et al., Topical Formulation of a New Plant Extract Complex with Refirming Properties. Clinical and Non-Invasive Evaluation in a Double-Blind Trial, International Journal of Cosmetic Science, 2000, vol. 22, pp. 201-206.
Morales, M.E. et al., Study and Description of Hydrogels and Organogels as Vehicles for Cosmetic Active Ingredients, J. Cosmet. Sci., 2009, vol. 60, pp. 627-636.
Saraf, S. et al., Development of Photochemoprotective Herbs Containing Cosmetic Formulations for Improving Skin Properties, J. Cosmet. Sci., 2012, vol. 63, pp. 119-131.
Takahashi, M. et al., Liposomes Encapsulating Aloe vera Leaf Gel Extract Significantly Enhance Proliferation and Collagen Synthesis in Human Skin Cell Lines, J. Oleo Sci., 2009, vol. 58, No. 12, pp. 643-650.
Wu, F. et al., Identification of Major Active Ingredients Responsible for Burn Wound Healing of Centella asiatica Herbs, Evidence-based Complementary and Alternative Medicine, 2012, available at https://www.ncbi.nlm.nih.gov/pmc/articles/PMC3546525/.

* cited by examiner

*Primary Examiner* — Michael Barker

(57) ABSTRACT

The disclosure is directed towards a highly emollient, plant-based moisturizer which noticeably reduces the visible signs of aging and effects of environmental impact. With one daily application, the formula reaches deep into the cellular structures to hydrate skin, delivering a luminous, porcelain effect on all skin types and ages. In an embodiment, the emulsion is provided in the form of a skin cream effective for reducing the visible signs of aging and effects of environmental impact. The skin cream formulation includes a mixture of at least one member of the genus of flowering plants known as *Convallaria*, an amphiphilic material, such as lecithin, *Centella* (*Centella asiatica* or *C. Asiatica*), an essential oil such as Myrrh; a product derived from *aloe*, a whole or reconstituted milk formulation, and a mineral clay, in amounts effective to reduce such signs of aging and environmental impact.

3 Claims, 3 Drawing Sheets

ANTI-AGING MOISTURIZING EMULSION

FIELD OF THE INVENTION

The present invention relates to the field of cosmetic or dermatological skin care treatment compositions, particularly to a topical anti-aging moisturizing emulsion, more particularly to a skin cream effective for reducing the visible signs of aging and effects of environmental impact, and most particularly to an emulsion containing at least one species of *Convallaria*, at least one amphiphilic material, such as a lecithin, *Centella* (*Centella asiatica* or *C. Asiatica*), Myrrh, *Aloe*, a mineral clay, and a whole or reconstituted milk formulation, in amounts effective to reduce such signs of aging and environmental impact.

BACKGROUND OF THE INVENTION

The skin of a human is a composite material of the epidermis and the dermis. The topmost part of the epidermis is the stratum corneum, which is the stiffest layer of the skin, as well as the one most affected by the surrounding environment. Below the stratum corneum is the internal portion of the epidermis. Below the epidermis, the topmost layer of the dermis is the papillary dermis, which is made of relatively loose connective tissues that define the micro-relief of the skin. The reticular dermis, disposed beneath the papillary dermis, is tight, connective tissue that is spatially organized. The reticular dermis is also associated with coarse wrinkles. At the bottom of the dermis lies the subcutaneous layer.

The skin's major functions include protection, excretion, secretion, absorption, thermoregulation, pigmentogenesis, accumulation, sensory perception, and regulation of immunological processes. These functions can be detrimentally affected by many structural changes in the skin, such as aging, disease, or exposure to solar radiation, pollution, and other factors present in the environment. The physiological changes generally associated with skin aging may include impairment of the barrier function and decreased turnover of epidermal cells.

Mechanical properties of the skin, for example elasticity, are controlled by the density and geometry of the network of collagen and elastic fiber tissue therein. Damaged collagen and elastin lose their contractile properties, resulting in skin wrinkling and skin surface roughness. As the skin ages or becomes unhealthy, it acquires sags, stretch marks, bumps, bruises or wrinkles. Further, it roughens, and its ability to synthesize Vitamin D decreases. Aged skin also becomes thinner and has a flattened dermoepidermal interface because of the alterations in collagen, elastin, and glycosaminoglycans.

DESCRIPTION OF THE PRIOR ART

U.S. Pat. No. 6,544,530 discloses a stable oil-in-glycerin emulsion containing at least one oil, at least one emulsifier and glycerin, topical anti-inflammatory activity, topical anti-fungal activity, topical anti-bacterial activity, topical anti-parasitic activity, and topical anti-viral activity, wherein botanical material can include myrrh and *aloe vera*, blended at high speed.

U.S. Published Patent Application 2013/0225497 discloses a skin collagen production-promoting agent that includes a milk protein fraction derived from milk, such as bovine milk, human milk, goat milk, ewe milk or the like.

U.S. Pat. No. 8,551,509 discloses a skin agent for external use containing salts of ubiquinone derivatives, that can further incorporate natural surfactants such as saponin, lecithin, soybean phospholipid, etc.; powders and color materials such as kaolin, silicic anhydride, aluminum magnesium silicate, etc.; plant extracts such as *aloe* and lily extract; and essential oils, such as Myrrh.

U.S. Published Patent Application 2013/0171283 teaches a composition, and method for its use, that may include *Centella asiatica, Vitis vinifera* seed, *Magnolia* bark, *Camellia sinensis*, and/or dihydroxymethylchromone; and may further include a moisturization agent, a UV absorbing agent, an anti-oxidant, a structuring agent, an emulsifier, a silicone containing compound, an essential oil (myrrh oil), a thickening agent, and a preservative.

U.S. Published Patent Application 2006/0024339 is directed toward a composition and method for controlling redness and aged or damaged skin, which may contain lecithin, phosphatidycholine, or choline that can be used in an amount ranging from about 0.5 to 50 weight percent. Moisturizers are typically present in an amount ranging from about 0.01 to 20 weight percent.

U.S. Pat. No. 8,470,350 discloses a cosmetic composition that includes a ready-to-mix mixture of ingredients including particles from dried herbs and/or flowers, a dried food, an essential oil, and kaolin; and may further include water, milk, and yogurt; for application as a facial treatment mask to skin in need thereof.

U.S. Published Patent Application 2014/0018328 discloses a clear, greaseless composition which includes a pharmaceutically active component, soothing actives such as gotu kola, moisturizers, emollients, fragrances preservatives and sugars.

The prior art, however, does not teach a skin cream effective for reducing the visible signs of aging and effects of environmental impact, and most particularly fails to teach an emulsion containing a species of *convallaria*, at least one amphiphilic material, such as a lecithin, *centella* (*Centella asiatica* or *C. Asiatica*), Myrrh, *Aloe*, a mineral clay, and a whole or reconstituted milk formulation, in amounts effective to reduce such signs of aging and environmental impact.

SUMMARY OF THE INVENTION

The present invention is directed towards a highly emollient, plant-based moisturizer which noticeably reduces the visible signs of aging and effects of environmental impact. With one daily application, the formula reaches deep into the cellular structures to hydrate skin, delivering a luminous, porcelain effect on all skin types and ages.

In one embodiment, the emulsion is provided in the form of a skin cream, topically applied, and effective for reducing the visible signs of aging and effects of environmental impact. The skin cream formulation includes a mixture of at least one member of the genus of flowering plants known as *convallaria*; an amphiphilic material, illustrated by, albeit not limited to lecithin; *Centella* (*Centella asiatica* or *C. Asiatica*); an essential oil, illustrated by, albeit not limited to Myrrh; a product derived from *aloe*, for example *aloe* vera gel; a whole or reconstituted milk formulation; and a mineral clay, in amounts effective to reduce such signs of aging and environmental impact.

The skin cream harnesses plant extracts rich in amino acids, fatty acids and phytochemicals. These materials, in combination, are effective to calm inflammation, speed wound healing, fortify collagen, improve circulation and stimulate cell growth. The formulation contains saponins and terpenoids, which act to heal the skin by boosting antioxidants, growing blood supply and strengthening the skin's layers.

Accordingly, it is an objective of the instant invention to provide a composition for preventing or alleviating visible signs of aging and effects of environmental impact.

It is another objective of the instant invention to provide a skin care composition that provides a method for the prevention, amelioration or treatment of pathological conditions of the skin, including but not limited to intrinsic or chronological aging, and aging due to the effects of environmental impact, illustrated by, albeit not limited to, sun damage (photoaging).

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

Definitions

Figure 1A:
FIG. 1A illustrates the left lateral aspect of a female patient's eye prior to treatment with the anti-aging moisturizing emulsion of Table 3.

As used herein, the term "*Convallaria*" refers to a genus of flowering plants. The genus includes 3 species of *Convallaria*, including *Convallaria majalis, Convallaria keiskei* and *Convallaria montana*. The most prevalent species is Lily Of The Valley. The invention contemplates the use of species of *convallaria* either singly or in any combination.

As used herein, the term "Lecithin" (from the Greek lekithos (egg yolk)) is a generic term which includes a group of amphiphilic yellow-brownish fatty substances occurring in animal and plant tissues. While lecithins are usually phospholipids, composed of phosphoric acid with choline, glycerol or other fatty acids usually glycolipids or triglyceride. The term "lecithins" is also understood to include lecithins which contain Glycerophospholipids such as phosphatidylcholine, phosphatidylethanolamine, phosphatidylinositol, phosphatidylserine, and phosphatidic acid. Further included are hydrolysed lecithins, which are hydrolysed enzymatically such that a portion of the phospholipids have one fatty acid removed by phospholipase. Such phospholipids are called lysophospholipids. Additionally, included are lecithins modified by a process called fractionation. During this process, lecithin is mixed with an alcohol, usually ethanol, ultimately resulting in a phosphatidylcholine-enriched lecithin fraction. The invention contemplates the use of species of lecithins either singly or in any combination.

As used herein, the term "*Centella asiatica*", (*C. asiatica*) commonly known as *centella* and gotu kola, includes any species of a small, herbaceous, frost-tender perennial plant of the family Mackinlayaceae or subfamily Mackinlayoideae of family Apiaceae, and is native to wetlands in Asia. It is used as a medicinal herb in Ayurvedic medicine, traditional African medicine, and traditional Chinese medicine. It is also known as the Asiatic pennywort or Indian pennywort in English, among various other names in other languages. In traditional herbal medicine, *C. asiatica* has been used for varicose veins, chronic venous insufficiency, psoriasis, minor wounds, strangury, and to encourage lactation. The invention contemplates the use of species of *C. asiatica* either singly or in any combination.

As used herein, the term "Myrrh" generally refers to a fragrant gum resin obtained from a number of small, thorny tree species of the genus *Commiphora*, which is an essential oil, termed an oleoresin, which generally contains about 2% to 10% of a volatile oil composed predominantly of sesquiterpenes, sterols, and steroids. The water-soluble gum portion (30% to 60%) contains polysaccharides and proteins as well as ethanol-soluble resins (25% to 40%). The resin is used, especially in the Near East, in perfumery, medicines, and incense. Sources include any of *Commiphora myrrha* (T. Nees) Engl., *Commiphora abyssinica* (Bevg.) Engl., or *Commiphora molmol* Engl. Family: Burseraceae. Myrrh has also been used as an astringent, as an antiseptic to be applied to inflamed lesions of the throat and mouth, as an emmenagogue, an antispasmodic, and for the treatment of cancer and infectious diseases. The invention contemplates the use of species of *Commiphora* either singly or in any combination.

As used herein, the term "*Aloe*" or "*Aloe Vera*" refers to the gel of a cactus-like succulent plant species of the genus *Aloe*. The species has a number of synonyms: *A. barbadensis* Mill., *Aloe* indica Royle, *Aloe perfoliata* L. var. *vera* and *A. vulgaris* Lam. It grows wild in tropical climates around the world and is cultivated for agricultural and medicinal uses. The *Aloe vera* plant has been used for thousands of years to heal a variety of conditions, most notably burns, wounds, skin irritations, and constipation. *Aloe* produces two substances, gel and latex, which are useful for various medicinal purposes. *Aloe vera* leaves contain phytochemicals, such as acetylated mannans, polymannans, anthraquinone C-glycosides, anthrones, other anthraquinones, such as emodin, and various lectins. *Aloe vera* gel is the clear, jelly-like substance found in the inner part of the *aloe* plant leaf. *Aloe vera* gel also contains substances known as glycoproteins and polysaccharides. Glycoproteins speed the healing process by stopping pain and inflammation while polysaccharides stimulate skin growth and repair. The invention contemplates the use of any species or form of *Aloe* either singly or in any combination.

As used herein, the term "Milk Formulation" is illustrated by, albeit not limited to, bovine milk, human milk, goat milk, ewe milk or the like. Such milk formulation may be used without additional treatment, or in the form of one or more of a reconstituted milk formulation, a skim milk formulation, whey, or the like. The invention contemplates the use of any species or form of Milk Formulation either singly or in any combination.

As used herein, the term "Mineral Clay" is understood to include hydrous aluminium phyllosilicates, sometimes with variable amounts of iron, magnesium, alkali metals, alkaline earths, and other cations, which are generally members of either the Kaolin group, Smectite group, Illite group, or Chlorite group.

The Kaolin group includes the minerals kaolinite, dickite, halloysite, and nacrite (polymorphs of $Al_2Si_2O_5(OH)_4$), and the kaolinite-serpentine group. The Smectite group includes dioctahedral smectites such as montmorillonite (bentonite), nontronite and beidellite and trioctahedral smectites for example saponite. The Illite group includes the clay-micas. Illite is the only common mineral. The Chlorite group includes a wide variety of similar minerals with considerable chemical variation. Other 2:1 clay types exist which are also useful in the present invention, such as sepiolite or attapulgite, clays with long water channels internal to their structure.

In certain embodiments kaolinite, a clay mineral with the chemical composition $Al_2Si_2O_5(OH)_4$ is used.

In certain embodiments, bentonite, an absorbent aluminium phyllosilicate clay consisting mostly of montmorillonite, is used. The different types of bentonite are each named after their respective dominant element, such as potassium (K), sodium (Na), calcium (Ca), and aluminium (Al). For industrial purposes, two main classes of bentonite are generally utilized—sodium and calcium bentonite. The invention contemplates the use of any species or form of Mineral Clay either singly or in any combination.

As used herein, an "effective amount" of a composition as described in some embodiments herein can be a quantity sufficient to achieve a desired therapeutic and/or prophylactic effect, for example, a requisite amount for the prevention of, or a reduction in the visible signs of aging and effects of environmental impact on the skin. The amount of composition administered to the subject can depend on the type and severity of the condition and on the characteristics of the individual, such as general health, age, and sex. A person skilled in the art will be able to determine appropriate dosages depending on these and other factors. Typically, an effective amount of the compositions described herein can be sufficient for achieving a therapeutic or prophylactic effect.

The use of numerical values in the various quantitative values specified throughout this disclosure, unless expressly indicated otherwise, are stated as approximations as though the minimum and maximum values within the stated ranges were both preceded by the word "about" unless expressly stated otherwise. In this manner, equivalent variations from a stated value can be used to achieve substantially the same results as the stated value. Also, the disclosure of ranges is intended as a continuous range including every value between the minimum and maximum values recited as well as any ranges that can be formed by such values. Also disclosed herein are any and all ratios (and ranges of any such ratios) that can be formed by dividing a recited numeric value into any other recited numeric value. Accordingly, the skilled person will appreciate that many such ratios, ranges, and ranges of ratios can be unambiguously derived from the numerical values presented herein and in all instances, such ratios, ranges, and ranges of ratios represent various embodiments of the present invention.

It should be noted that in all of the embodiments comprising compositions described herein, the total of all ingredients comprising the composition does not exceed 100%.

EMBODIMENTS OF THE INVENTION

In an embodiment, the topical anti-aging moisturizing emulsion contains at least one species of *Convallaria*, at least one amphiphilic material, such as a lecithin, *Centella* (*Centella asiatica* or *C. Asiatica*), Myrrh, a product derived from aloe—for example aloe vera gel, a mineral clay, and a whole or reconstituted milk formulation, in amounts effective to reduce such signs of aging and environmental impact.

Exemplary Skin Cream formulations will generally fall within the formulations outlined in Table 1:

TABLE 1

| INGREDIENT | % (WT/WT) |
|---|---|
| Lecithin | about 45 to about 55 |
| Aloe | about 40 to about 50 |
| Myrrh | about 1 to about 3 |
| *Centella asiatica* | about 1 to about 3 |
| *Convallaria* (one or more species) | about 0.1 to about 0.99 |
| Mineral Clay | about 0.1 to about 0.99 |
| Powdered Milk Formulation | about 0.1 to about 0.99 |

An illustrative, albeit non-limiting embodiment, exemplifying a specific formulation is shown in Table 2:

TABLE 2

| INGREDIENT | % (WT/WT) |
|---|---|
| 60 cc Lecithin | about 51 |
| 50 cc Aloe | about 42 |
| 1 gm powdered goat's milk | about 0.8 |
| 1 gm kaolin powder | about 0.8 |
| 2.5 cc Myrrh (*Commiphora abyssinica*) | about 2.1 |
| 2.5 cc Gotu Kola (*Centella asiatica*) | about 2.1 |
| 1 cc Lily of Valley (*Convallaria*) | about 0.8 |

A further illustrative, albeit non-limiting embodiment, exemplifying a specific formulation is shown in Table 3:

TABLE 3

| INGREDIENT | % (WT/WT) |
|---|---|
| 60 cc Lecithin | about 51 |
| 50 cc Aloe | about 42 |
| 1 gm powdered goat's milk | about 0.8 |
| 1 gm bentonite powder | about 0.8 |
| 2.5 cc Myrrh (*Commiphora abyssinica*) | about 2.1 |
| 2.5 cc Gotu Kola (*Centella asiatica*) | about 2.1 |
| 1 cc Lily of Valley (*Convallaria*) | about 0.8 |

The formulation is produced by mixing the ingredients until a final emulsion is formed.

EXAMPLES

Example 1

A 65-year-old female patient with extensive wrinkling and crow's feet surrounding her eyes, was treated with a formulation as illustrated in Table 3. The initial treatment was for a ten-day period, subsequent to which a follow-up appointment was scheduled two months later.

FIG. 1A illustrates the left lateral aspect of the female patient's eye prior to treatment with the anti-aging moisturizing emulsion of Table 3.

Figure 1B:
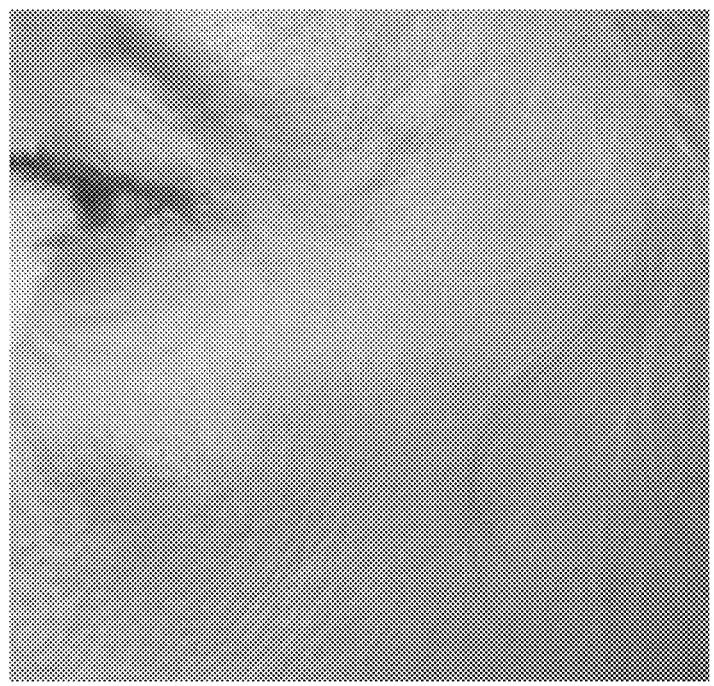
FIG. 1B illustrates the left lateral aspect of a female patient's eye subsequent to treatment with the anti-aging moisturizing emulsion of Table 3.

FIG. 1B illustrates the left lateral aspect of the female patient's eye subsequent to treatment with the anti-aging moisturizing emulsion of Table 3.

Even after a two-month hiatus, without further treatment, a significant reduction in wrinkles and crow's feet is apparent.

Example 2

A 45-year-old male patient with extensive wrinkling and crow's feet surrounding his eyes, was treated with a formulation as illustrated in Table 3. The initial treatment was for a fourteen-day period, subsequent to which a follow-up appointment was scheduled one week later.

Figure 2A:
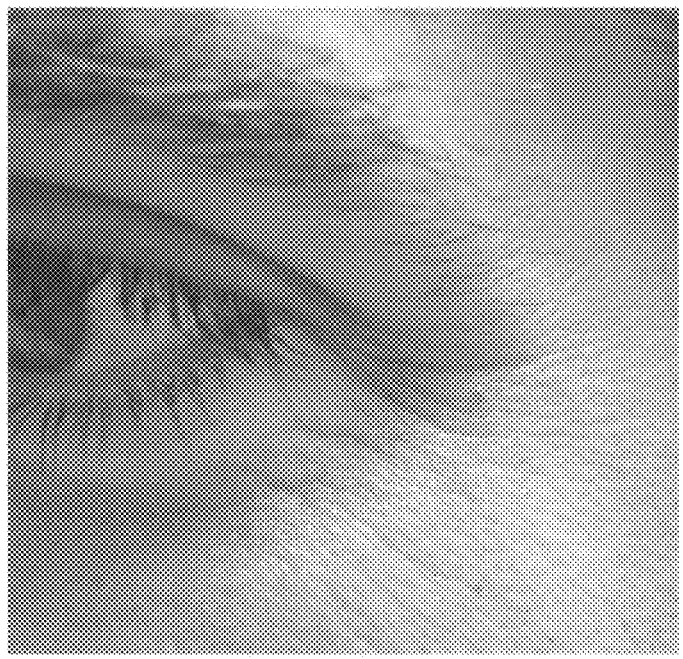
FIG. 2A illustrates the left lateral aspect of a male patient's eye prior to treatment with the anti-aging moisturizing emulsion of Table 3.

FIG. 2A illustrates the left lateral aspect of the male patient's eye prior to treatment with the anti-aging moisturizing emulsion of Table 3.

Figure 2B:
FIG. 2B illustrates the left lateral aspect of a male patient's eye subsequent to treatment with the anti-aging moisturizing emulsion of Table 3.

FIG. 2B illustrates the left lateral aspect of the male patient's eye subsequent to treatment with the anti-aging moisturizing emulsion of Table 3.

A significant reduction in wrinkles and crow's feet is apparent.

Example 3

A 75-year-old male patient, suffering from diabetes, had extensive scaling on the epidermis of both lower legs. The formulation as illustrated in Table 3, was applied to one leg for 10 days, after which the epidermis of both legs was compared.

Figure 3A:
FIG. 3A illustrates a side-by-side comparison of the anterior frontal aspect of the epidermis of a male patient's treated and untreated lower leg.

FIG. 3A illustrates a side-by-side comparison of the anterior frontal aspect of the epidermis of the patient's treated and untreated lower leg.

Figure 3B:
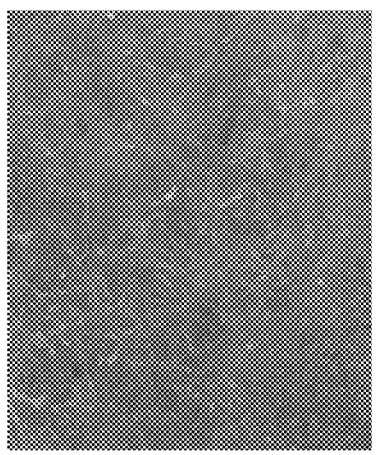
FIG. 3B illustrates a close-up view of the anterior frontal aspect of the epidermis of a male patient's untreated lower leg.

FIG. 3B illustrates a close-up view of the anterior frontal aspect of the epidermis of a male patient's untreated lower leg.

Figure 3C:
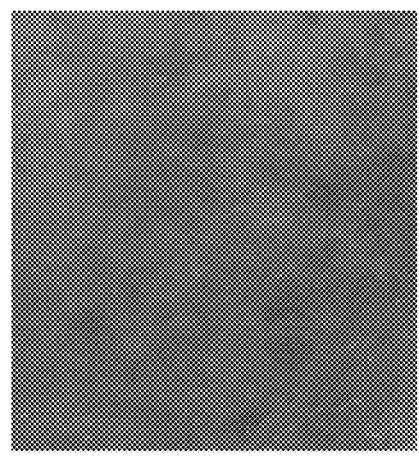
FIG. 3C illustrates a close-up view of the anterior frontal aspect of the epidermis of a male patient's lower leg subsequent to treatment with the anti-aging moisturizing emulsion of Table 3.

FIG. 3C illustrates a close-up view of the anterior frontal aspect of the epidermis of a male patient's lower leg subsequent to treatment with the anti-aging moisturizing emulsion of Table 3.

It is noted that the scaling on the treated leg has been markedly reduced as a result of the treatment.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A skin cream emulsion effective for reducing the visible signs of aging and effects of environmental impact, said cream emulsion comprising, in combination:
   about 45% to about 55% (wt/wt) Lecithin,
   about 40% to about 50% (wt/wt) *Aloe*,
   about 1% to about 3% (wt/wt) Myrrh,
   about 1% to about 3% (wt/wt) *Centella asiatica*,
   about 0.1% to about 0.99% (wt/wt) of at least one species of *Convallaria*,
   about 0.1% to about 0.99% (wt/wt) Mineral Clay, and
   about 0.1% to about 0.99% (wt/wt) of a Powdered Milk Formulation.

2. The skin cream emulsion of claim 1 wherein said composition comprises, in combination:
   about 51% (wt/wt) Lecithin,
   about 42% (wt/wt) *Aloe*,
   about 2.1% (wt/wt) Myrrh,
   about 2.1% (wt/wt) *Centella asiatica*,
   about 0.8% (wt/wt) Lily of the Valley,
   about 0.8% (wt/wt) kaolin powder, and
   about 0.8% (wt/wt) powdered goat's milk.

3. The skin cream emulsion of claim 1 wherein said composition comprises, in combination:
   about 51% (wt/wt) Lecithin,
   about 42% (wt/wt) *Aloe*,
   about 2.1% (wt/wt) Myrrh,
   about 2.1% (wt/wt) *Centella asiatica*,
   about 0.8% (wt/wt) Lily of the Valley,
   about 0.8% (wt/wt) bentonite powder, and
   about 0.8% (wt/wt) powdered goat's milk.

\* \* \* \* \*